US012740957B2

(12) United States Patent
Wolfe et al.

(10) Patent No.: US 12,740,957 B2
(45) Date of Patent: Sep. 22, 2026

(54) COMPOSITION AND METHOD TO REDUCE LIVER FAT AND CIRCULATING TRIACYLGLYCEROLS

(71) Applicant: The Amino Company LLC, Los Angeles, CA (US)

(72) Inventors: Robert R. Wolfe, Norwich, CT (US); Melanie Giselle Cree, Aurora, CO (US); Frederick L. Wolfe, Rancho Mirage, CA (US)

( * ) Notice: Subject to any disclaimer, the term of this patent is extended or adjusted under 35 U.S.C. 154(b) by 574 days.

(21) Appl. No.: 18/202,285

(22) Filed: May 26, 2023

(65) Prior Publication Data

US 2024/0390312 A1 Nov. 28, 2024

(51) Int. Cl.

| | |
|---|---|
| ***A61K 31/198*** | (2006.01) |
| ***A61K 9/00*** | (2006.01) |
| ***A61K 31/4172*** | (2006.01) |
| ***A61P 1/16*** | (2006.01) |

(52) U.S. Cl.

CPC .......... *A61K 31/198* (2013.01); *A61K 9/0095* (2013.01); *A61K 31/4172* (2013.01); *A61P 1/16* (2018.01)

(58) Field of Classification Search

CPC ...... A61K 31/198; A61K 31/4172; A61P 1/16
See application file for complete search history.

(56) References Cited

U.S. PATENT DOCUMENTS

| | | | | |
|---|---|---|---|---|
| 11,412,771 B2 * | 8/2022 | Wolfe | .................. | A23L 33/175 |
| 11,752,112 B2 * | 9/2023 | Wolfe | .................. | A61K 9/0056 424/439 |

FOREIGN PATENT DOCUMENTS

| | | | | |
|---|---|---|---|---|
| WO | WO-2008134645 A1 * | 11/2008 | ........... | A23L 33/175 |

* cited by examiner

*Primary Examiner* — Kevin E Weddington
(74) *Attorney, Agent, or Firm* — 928

(57) ABSTRACT

The present invention relates to amino acid compositions and methods to reduce liver fat and circulating concentration of triacylglycerol. The invention further relates to amino acid compositions for reducing liver fat and circulating triacylglycerol (TG) in individuals with hepatic steatosis (HS). The compositions described herein are pharmaceutical or nutritional compositions. The compositions are based on a specially formulated mixture of essential amino acids (EAAs).

20 Claims, No Drawings

COMPOSITION AND METHOD TO REDUCE LIVER FAT AND CIRCULATING TRIACYLGLYCEROLS

FIELD OF THE DISCLOSURE

Embodiments of the present disclosure relate to amino acid composition and methods to reduce liver fat and circulating concentration of triacylglycerol.

BACKGROUND OF THE DISCLOSURE

Hepatic steatosis (HS) develops due to an imbalance in the triglyceride/fatty acid (TG/FA) cycle. The TG/FA cycle involves cycling of fatty acids from adipose tissue to the liver and back. The development of HS involves disruption of one or more of the components of the TG/FA cycle. Under normal conditions fatty acids stored in adipose tissue as triglycerides are released into plasma as free fatty acids (FFA) at a rate in excess of the requirement for substrate oxidation. Clearance of plasma FFA by most tissues and organs is directly related to their oxidative metabolism in those tissues and organs, but FFA are cleared by the liver at a rate in excess of the rate of hepatic fatty acid oxidation. Hepatic fatty acids may also arise from de novo lipogenesis. Some hepatic fatty acids are oxidized, while those that are not oxidized are packaged into triglycerides and secreted into the plasma, largely in the form of very low-density lipoprotein-triglycerides (VLDL-TG). The TG/FA cycle is completed by the enzymatic hydrolysis of circulating VLDL-TG by lipoprotein lipase (LPL) in adipose tissue and uptake and re-esterification into triglycerides of the resultant fatty acids.

There are multiple possible sites of disruption of the normal functioning of the TG/FA that can lead to HS, including:

1) Excessive hydrolysis of adipose tissue triglycerides and release of FFA into plasma. The rate of FFA release is directly related to the plasma concentration of FFAs, as well as to hepatic fatty acid uptake and production of triglycerides. Increased fat mass is the most common reason for increased lipolysis and release of FFA into the plasma. For this reason, guidelines for treatment of HS recommend weight reduction as an effective treatment, but long-term adherence to caloric restriction weight loss programs is low.
2) Accelerated de novo fatty acid synthesis. Although the rate of de novo lipid synthesis is low in the post-absorptive state in normal weight individuals, the rate can be rapidly activated in the fed state following carbohydrate ingestion and accelerated de novo synthesis is directly related to hepatic triglyceride accumulation.
3) Limited oxidative metabolism of fatty acids due to impaired mitochondrial function. For this reason, exercise is promoted as a treatment for excess fat in the liver. Exercise training increases the capacity for fatty acid oxidation, in part due to the increased number and function of mitochondria.
4) Insufficient secretion of VLDL-TG secretion into plasma to balance the rate of hepatic accumulation of triglycerides. VLDL-TG secretion may be limited by the synthesis of ApoB100, which is a protein necessary for the packaging of VLDL-TG for secretion into plasma.
5) Limited peripheral clearance of VLDL-TG by LPL contributing to elevated plasma VLDL-TG concentration, which in turn inhibits VLDL-TG secretion because of a greater concentration gradient between intra-hepatic and plasma VLDL-TGs.

Because of the complexity of the physiological interrelationships that can lead to HS, it is therefore reasonable to expect that a multi-modality approach based on normalizing all aspects of the physiological functioning of the TG/FA cycle is likely to be the most effective in normalizing the TG/FA cycle, thereby reducing liver fat and circulating triacylglycerol.

BRIEF SUMMARY OF THE DISCLOSURE

The present invention relates to amino acid compositions and methods to reduce liver fat and circulating concentration of triacylglycerol. The invention further relates to amino acid compositions for reducing liver fat and circulating triacylglycerol (TG) in individuals with hepatic steatosis (HS). The compositions described herein are pharmaceutical or nutritional compositions. The compositions are based on a specially formulated mixture of essential amino acids (EAAs).

DETAILED DESCRIPTION

An embodiment of the present invention includes a combination of specific amino acids capable of lowering liver fat content and circulating concentrations of TGs. It was discovered that that a formulation containing specific free essential amino acids (EAAs) is optimal for specifically targeting the TG/FA cycle liver and is effective in the absence of significant changes in body composition or insulin sensitivity.

One of the principal metabolic targets of the present formulation is to decrease hepatic fatty acid synthesis and improve fatty acid oxidation by decreasing the availability of methionine in the liver. Methionine is an essential amino acid (EAA) that universally initiates the translation of mRNA in the process of protein synthesis throughout the body and plays a variety of other beneficial metabolic roles as well. However, methionine also stimulates de novo hepatic fatty acid synthesis and inhibits fatty acid oxidation via transcriptional effects on relevant genes. As a result, restriction of dietary methionine intake in rodents decreases fat in the liver and extends lifespan. Unfortunately, restriction of methionine consumption in humans has not led to the same benefits as shown in experiments involving rodents. In addition to the impracticality of eliminating a single EAA from the diet, methionine deficiency may lead to a variety of adverse effects throughout the body, including inhibition of protein synthesis and decreased immune function.

The present formulations capitalize on the nature of the hepatic amino acid transporters to selectively reduce hepatic methionine availability without creating a systemic deficiency. The present formulations create a localized deficiency in hepatic methionine by competitively inhibiting methionine transport into the liver. Methionine is transported into the liver by the L amino acid transporter (LAT1) system. Leucine, lysine, isoleucine, valine, phenylalanine, threonine and histidine, all of which are contained in the present formulation, are also transported into the liver by the LAT1 system, while methionine is not included in the formulation. The increases in the portal vein concentrations of leucine, lysine, isoleucine, valine, phenylalanine, threonine and histidine after consumption of the present formulation competitively inhibit the hepatic uptake of endogenous methionine. The competitive inhibition of methionine uptake by the liver can achieve the beneficial effects of dietary restriction on hepatic fat accumulation without negatively impacting metabolic roles of methionine throughout the body as might be expected from true dietary restriction. As a result of the selective clearance by the liver of the absorbed EAAs from ingestion of the present formulation, and the corresponding inhibition of hepatic clearance of circulating methionine, the ratios of methionine to the other EAAs are higher in the hepatic venous blood than the portal venous blood. As a result, relatively normal rates of uptake of methionine are maintained in tissues and organs other than the liver, thereby avoiding any symptoms of deficiencies that may arise from true dietary restriction.

The present formulations contain multiple EAAs that are transported by the LAT1 transport system, rather than containing a larger dose of a single EAA that would accomplish the same purpose of competitive inhibition of methionine inward transport. The balanced mixture of EAAs has the important beneficial effect of stimulating protein synthesis, including hepatic protein synthesis, whereas increased availability of a single EAA cannot elicit the same response. In addition, stimulated protein synthesis can improve the capacity for fatty acid oxidation by producing the proteins required for increased mitochondrial biogenesis, which is activated by leucine. Further, stimulation of apolipoprotein B 100 (ApoB100) synthesis by the present invention may decrease hepatic TG accumulation by enhancing the packaging and secretion of VLDL-TG from the liver into the plasma. The selected EAAs in the present invention, particularly including leucine, activate mTORC1 and associated molecules involved in the initiation of protein synthesis, including the synthesis of ApoB100. Methionine availability is not normally rate-limiting for protein synthesis in the post-absorptive state because the recommended dietary allowance of methionine is significantly exceeded by a normal amount of dietary protein consumption. Since protein synthesis requires methionine and methionine is not included in the present invention, stimulation of protein synthesis by the present formulation will be sustained by increased utilization of endogenous stores of methionine. Increased availability of hepatic ApoB100 resulting from stimulated synthesis will facilitate packaging of VLDL-TG, thereby enabling more extensive export of triglycerides in the form of VLDL-TG from the liver into the plasma. In addition, increased utilization of endogenous methionine for protein synthesis will further reduce hepatic methionine availability, thereby further amplifying the beneficial effect of methionine restriction on hepatic fat accumulation.

The present formulations not only stimulate ApoB100 synthesis in the liver, but also stimulate protein synthesis throughout the body by activation of mTOR and increased precursor availability of EAAs that are normally rate-liming. The stimulation of protein synthesis by EAAs is not impaired by the presence of elevated fatty acids, and thus is effective in obesity. The specific profile of EAAs in the present formulations increase utilization of endogenous sources of all the amino acids not contained in the formulation as precursors for protein synthesis. Thus, stimulated protein synthesis not only reduces methionine availability, as described above, but also reduces the plasma concentrations of non-essential amino acids (NEAAS), including alanine and glutamine, since they are also absent in the present composition. Decreased availability of NEAAs limits substrate availability for gluconeogenesis and DNL, thereby tending to normalize control of glucose metabolism and decreasing HS.

An additional benefit of the present formulations is the reduction of liver inflammation, which will help to reduce liver fat and slow the progression of HS to non-alcoholic steatohepatitis (NASH and cirrhosis).

The present formulations are composed of the minimal number of EAAs that enable reduction in liver fat and lowering of circulating VLDL-TG by creating a selective reduction of methionine in the liver, but not throughout the rest of the body, while also stimulating the synthesis of the hepatic protein (ApoB100) needed to secrete VLDL-TG from the liver as well as the proteins required for mitochondrial biogenesis. The present formulations decrease fat accumulation in the liver and lower blood VLDL-TG concentration by one or more of the following mechanisms: decreasing de novo lipogenesis; increasing fatty acid oxidation in liver and throughout the body; increasing triglyceride secretion from the liver in the form of VLDL-TG; and increasing clearance of circulating VLDL-TG by activating lipoprotein lipase.

Method of the Invention

In an embodiment, the method of the invention comprises administering the amino acid compositions to an individual. In some embodiments, the composition may comprise the EAAs leucine, lysine, isoleucine, valine, phenylalanine, threonine and histidine. The amino acids can be selected from L-amino acids. In particular embodiments, the amino acids of the invention are free amino acids or amino acid salts. The compositions may comprise about 30-34% leucine, 9-13% valine, 9-13% isoleucine, 8-12% histidine, 8-12% phenylalanine, 14-18% lysine, and 8-12% threonine.

The dose of the EAA composition can vary depending on the body weight, sex, age, and/or medical condition of the individual. The composition may also be used in non-human species. Typical doses of the composition are about 5, 10, 15 or 20 gms, and may be taken once or multiple times per day. Multiple doses per day may be required. The timing and duration of administration may vary. For example, it may be taken between meals or with meals.

The composition is conventionally administered orally, but also may be given intravenously or via a nasogastric feeding tube. The amino acids may include an excipient of any non-toxic form, whereby the composition is microencapsulated.

The EAA composition may be given to any individual with a physical condition often associated with increased fat in the liver, including obesity, chronic alcohol consumption, aging, and metabolic diseases such as diabetes and polycystic ovary syndrome. The human subject may be any age, including children and aging individuals. The individual may be undergoing other treatment, such as bariatric surgery, caloric restriction weight loss, rehabilitation for alcohol abuse syndrome, and hormonal therapy.

In some embodiments liver fat may decrease 3, 5, 10, 15, 20, 25, 30, 35, 40, 45, or 50% compared to the pre-treatment level. Plasma total TG concentration (including free and VLDL-TG) may decrease 5, 10, 15, 20, 25, 30, 35, 40, 45, or 50% compared to the pre-treatment level.

EXAMPLES

Example 1—Reduction of Liver Fat and Circulating Triacylglycerol with an Essential Amino Acid-Based Composition Objective: To determine if dietary supplementation with our essential amino acid composition (EAAs) would decrease increased fat deposition in the liver (hepatic steatosis, HS) and reduce circulating triacylglycerol (TG) levels in female adolescents with poly cystic ovary syndrome (PCOS). The EAA composition administered to the study participants contained 32% leucine, 11% valine, 11% isoleucine, 10% histidine, 10% phenylalanine, 16% lysine, and 10% threonine in free form.

Background—Excess fat in the liver consists of a spectrum of disease stages from hepatic steatosis (HS) to non-alcoholic steatohepatitis; the latter of which can progress to cirrhosis and hepatocellular carcinoma. HS can occur because of excess alcohol consumption and also in the absence of alcohol consumption (nonalcoholic fatty liver disease, NAFLD). HS is anticipated to become the leading cause of liver transplants in the US. Obese females with poly cystic ovary syndrome (PCOS) are at particularly high risk of HS. PCOS is the most common reproductive endocrine disorder, affecting 5-10% of women and up to 20% of women with obesity. Experimental pharmacological interventions are often used to improve symptoms of HS, but no standard-of-care treatments exists for HS except lifestyle interventions (i.e., diet, exercise, and weight loss). The aim of this study was to determine if four weeks of twice daily EAA supplementation compared to a placebo supplement in adolescents with PCOS and obesity reduced liver fat, circulating, TGs, and liver inflammation. We also aimed to determine if EAAs directly affected the liver or if changes were secondary to body composition changes.

Methods—A double-blind, crossover, placebo-controlled trial was conducted in 21 adolescents with PCOS (BMI 37.3±6.5 kg/m$^2$, age 15.6±1.3y). Liver fat and circulating concentration of triacylglycerol (TG) were measured following each 28-day phase of placebo or EAA.

Overall study design—This was a double-blind, crossover, placebo-controlled study of adolescent girls with PCOS, obesity, and HS. Eligibility was determined at an initial screening visit after which participants were randomized to start phase 1 with either placebo or EAA within 2 months of the screening visit. After the end of the first four weeks (phase 1), there were four weeks of washout before the start of phase 2. During each phase, 15 grams of the EAAformulation or a placebo of calorically equivalent maltodextrin supplements were taken twice daily by mixing the powder into a liquid of the participant's choice. The placebo contained the same flavoring agent as in the EAA drink. Metabolic tests were conducted on the last 2 days of each phase of the intervention. On the morning of metabolic studies, no supplement or placebo were taken.

Participants—Participants were recruited from a multidisciplinary PCOS clinic, general endocrine clinic, and lifestyle intervention obesity clinics at Children's Hospital Colorado, Aurora, CO, USA. Inclusion criteria were female sex, aged 12-21, sedentary lifestyle (<2 hours of moderate exercise/week), obesity (BMI percentile >90% for age and sex), PCOS per the 2018 International PCOS guidelines (irregular menses >12 months post-menarche and clinical or biochemical hypertestosteronemia), and HS per FibroScan (502 Touch Echosens, Paris France; HS is a CAP score of >225). Exclusion criteria included use of medications known to affect insulin sensitivity (metformin, oral glucocorticoids within 10 days, atypical antipsychotics, immunosuppressant agents, HIV medications, hormonal contraceptives), pregnant or breastfeeding, severe illness requiring hospitalization within 60 days, diabetes (Hemoglobin A1C >6.4%), BMI percentile<90% for age and sex, weight <84 lbs or >325 lbs, anemia (hemoglobin <11 mg/dL), diagnosed major psychiatric or developmental disorder limiting informed consent, implanted metal devices not compatible with MRI, use of blood pressure medications, and known liver disease other than NAFLD or AST or ALT >125 IU/L. The study was approved by University of Colorado Anschutz Medical Campus Institutional Review Board and the Children's Hospital Colorado Research institute (18-0803, and clinical trials.gov NCT03717935). All participants 18-21 years of age provided written informed consent and for all participants aged <18 years of age, parents and participants provided written consent and assent. One participant withdrew following the screening visit and two participants withdrew after completing the first phase. Reasons for dropout were SARS-COV-2 related. Two participants were unable to have an MRI during their second phase (MRI data n=19).

Metabolic phenotyping—The last week of each phase, the participants underwent a number of procedures, including wearing an accelerometer (ActiGraph GT9X Link, Actigraph, Pensacola, FL) on their wrist for 7-days and completing a 3-day activity recall (35). On the day before the metabolic study, a DEXA scan (Horizon W, Apex 5.6.06, Waltham, MA) was performed to measure body composition including fat and lean mass and percentage. An MRI of the liver and abdomen was performed on a 3.0 Tesla Magnet (Siemens Magnetom Skyra) and abdominal visceral fat, subcutaneous fat (subQ), liver fat, and liver span measurements were collected. The hepatic fat fraction (liver fat %), visceral fat and subQ fat content were calculated as previously published. After the hepatic fat scan, hepatic $^{31}$phosphorus-magnetic resonance spectroscopy ($^{31}$P-MRS) data were collected. After the MRS, participants were sent home with a standardized evening meal and snack to control pre-study carbohydrate (CHO) intake.

Metabolic studies—Baseline labs, including samples to assess DNL via $D_2O$, were collected following a 12-hour fast. A Fibroscan was repeated, and indirect calorimetry was performed immediately prior to the start of an oral sugar tolerance test (OSTT) using a gas analyzer. The OSTT test drink was consumed within 5 minutes, with subsequent blood draws for 4 hours to assess the hormonal responses. Standard methods were used to analyze concentrations of plasma glucose, lipids, liver enzymes, and hormones.

Calculations and statistical analysis—Several measures of insulin sensitivity were calculated from the OSTTT test. HOMA-IR and Matsuda index were calculated, as was the oral minimal model insulin sensitivity (OMM Si) calculations, and OMM SI dynamics (SiD) using differential based equations (37). The PCOS-HS index was used to calculate the NAFLD probability (%) using BMI percentile, height, weight, age, waist circumference, and ALT and SHBG concentrations, as described in an earlier publication. The Shapiro-Wilk test was used to test for normality. Paired t-tests, for parametric data, and Wilcoxon matched-pairs signed rank tests, for non-parametric data, were performed to compare participants EAA arm to their placebo arm of the study and the median and 25$^{th}$ and 75$^{th}$ percentiles are presented. For variables that were normally distributed, data are presented as means±SD. Wilcoxon signed rank tests were used to assess relative change variables relative to the no change value of 0. For OSTT curves of glucose, insulin, FFA and glycerol and measures of lipogenesis, data were analyzed by repeated-measures ANOVA with time and treatment effects, corrected for multiple comparisons and presented as mean±SE. All calculations were performed in PRISM (9.5.1) or Excel (2019, version 2212). A P-value<0.050 was considered significant and P<0.100 considered a trend.

Results—Compared to placebo, EAAs was associated with no difference in body weight (P>0.673). Two markers of liver health improved-HS was lower (−0.8% absolute, −7.5% relative reduction, P=0.013), as was plasma aspartate amino transferase (AST), an indicator of liver inflammation (−8%, P=0.004). Plasma-TG (−9%, P=0.015) and VLDL-TG (−21%, P=0.031) were reduced as well. Dietary supplementation with EAAs in adolescents with PCOS significantly lowered liver fat, decreased liver inflammation, and reduced plasma triacylglycerol concentration as compared to placebo.

Body composition, fasting biochemistries, and hormones: Both placebo and EAA were well tolerated with a compliance of 96% and 93%, respectively. Anthropometric measurements including height, weight, BMI, and waist-hip ratio were unchanged with EAA supplement. Upon entry into the study 62% of the girls had HS as measured by MRI (HS>5% by volume, n=13/21). Compared to the amount of liver fat with placebo use (8%), liver fat was significantly lower following EAA supplementation (7.3%, P=0.020), with no significant changes in physical activity or total energy consumption per day, and energy derived from protein, fat and carbohydrate oxidation were unchanged.

Blood biochemistries: Fasting plasma-TG concentration was significantly lower by 13 mg/dL with EAA (P=0.015). Similar to the reduction in serum total TGs, fasting VLDL-TG concentration was 21% lower with EAA supplementation (P=0.031). Further, the peak absolute quantity of VLDL-TG achieved following the OSTT stimulus was also 21% significantly lower during the EAA phase. The absolute area-under-the-curve (aAUC) of VLDL-TG concentration vs measurement interval was significantly less (P=0.001 with EAA consumption than placebo. Serum AST, a clinical index of liver inflammation, was 8% lower on EAA (P=0.004), and total testosterone was 15% lower with EAA, although this did not reach significance (P=0.093).).

Liver phosphorous metabolites: Compared to placebo, γATP was significantly higher (P=0.044; following EAA supplementation, representing greater hepatic energy metabolism at the time of measurement. Membrane PE/TP reflecting cell turnover tended to be higher (P=0.060) and the ratio of PC/PE tended to be lower (P=0.068) in the EAA visit compared to placebo control.

Conclusion—The present blinded, crossover study investigated the effect of a daily EAA-based dietary supplement, taken for 4 weeks, on HS in adolescents with obesity and PCOS. Compared to placebo, following EAA supplementation, we observed significant reductions in plasma-TG and VLDL-TG concentrations and levels of AST, a marker of liver inflammation. Most importantly, liver fat was significantly lower on the EAA supplement. Surprisingly, the treatment specifically targeted the liver, as the reduction in liver fat occurred in the absence of other changes in diet or activity level, either of which could have potentially affected liver fat independently of a direct effect of EAAs on the liver.

Thus, there has been described a composition and method of using the composition to selectively reduce hepatic methionine availability without creating a systemic deficiency and to reduce liver fat and circulating triacylglycerol (TG) in individuals with hepatic steatosis (HS). It is apparent to those skilled in the art, however, that many changes, clarifications, modifications, other uses, and applications for the composition and method of using are possible, and also such changes, variations, modifications, other uses, and application which do not depart from the spirit and scope of the invention are deemed to be covered by the invention, which is limited only by the claims which follow.

What is claimed is:

1. A composition to reduce liver fat and circulating concentration of triacylglycerol comprising an amount of the free essential amino acids (EAAs) composition, wherein the EAAs composition consists of from about 30% to about 34% leucine, from about 9 to about 13% valine, from about 9 to about 13% isoleucine, from about 8 to about 12% histidine, from about 8 to about 12% phenylalanine, from about 14 to about 18% lysine, and from about 8 to about 12% threonine of the EAAs composition by weight.

2. The composition of claim 1, wherein doses of the composition are about 5, 10, 15 or 20 gms.

3. The composition of claim 1, wherein the amino acids of the composition are in free form and/or salt form.

4. The composition of claim 1, wherein the composition comprises 32% leucine, 11% valine, 11% isoleucine, 10% histidine, 10% phenylalanine, 16% lysine, and 10% threonine in free form.

5. The composition of claim 1, further comprising at least one excipient.

6. The composition of claim 1, wherein the composition is formulated into a tablet, capsule, powder, food product, or liquid.

7. The composition of claim 1, wherein the composition is microencapsulated.

8. A method of reducing liver fat and circulating concentration of triacylglycerol comprising administering a free essential amino acids (EAAs) composition, wherein the EAAs composition consists of from about 30% to about 34% leucine, from about 9 to about 13% valine, from about 9 to about 13% isoleucine, from about 8 to about 12% histidine, from about 8 to about 12% phenylalanine, from about 14 to about 18% lysine, and from about 8 to about 12% threonine of the EAAs composition by weight.

9. The method of claim 8, wherein the subject is a mammal.

10. The method of claim 9, wherein the mammal is a human.

11. The method of claim 8, wherein the composition is administered once a day.

12. The method of claim 8, wherein the composition is administered multiple times a day.

13. The method of claim 8, wherein the composition is taken with meals.

14. The method of claim 8, wherein the composition is administered orally.

15. The method of claim 8, wherein the composition is administered intravenously or via nasogastric feeding tube.

16. The method of claim 8, wherein the composition is administered to an individual with a physical condition associated with increased fat in the liver.

17. The method of claim 16, wherein the condition associated with fat in the liver comprises obesity, chronic alcohol consumption, aging, type 2 diabetes or poly cystic ovary syndrome.

18. A method of reducing liver fat and circulating concentration of triacylglycerol comprising administering a free essential amino acids (EAAs) composition, wherein the EAAs composition consists of 32% leucine, 11% valine, 11% isoleucine, 10% histidine, 10% phenylalanine, 16% lysine, and 10% threonine in free form of the EAAs composition by weight.

19. The method of claim 18, wherein the subject is a mammal.

20. The method of claim 19, wherein the mammal is a human.

* * * * *